(12) United States Patent
Leszinske

(10) Patent No.: US 9,936,904 B2
(45) Date of Patent: Apr. 10, 2018

(54) METHOD AND APPARATUS FOR AUTOMATED MEASUREMENT OF CHIRAL ANALYTE CONCENTRATION

(71) Applicant: Alan J. Leszinske, Albuquerque, NM (US)

(72) Inventor: Alan J. Leszinske, Albuquerque, NM (US)

( * ) Notice: Subject to any disclaimer, the term of this patent is extended or adjusted under 35 U.S.C. 154(b) by 619 days.

(21) Appl. No.: 14/405,187

(22) PCT Filed: Jun. 3, 2013

(86) PCT No.: PCT/US2013/043914
§ 371 (c)(1),
(2) Date: Dec. 3, 2014

(87) PCT Pub. No.: WO2013/184584
PCT Pub. Date: Dec. 12, 2013

(65) Prior Publication Data
US 2015/0157246 A1 Jun. 11, 2015

Related U.S. Application Data

(60) Provisional application No. 61/655,806, filed on Jun. 5, 2012.

(51) Int. Cl.
*A61B 5/1455* (2006.01)
*A61B 5/145* (2006.01)
(Continued)

(52) U.S. Cl.
CPC ........ *A61B 5/14532* (2013.01); *A61B 5/1455* (2013.01); *A61B 5/1459* (2013.01); *A61B 5/1495* (2013.01); *A61B 5/14558* (2013.01); *A61B 5/153* (2013.01); *A61B 5/15003* (2013.01); *A61B 5/155* (2013.01); *A61B 5/150229* (2013.01); *A61B 5/150992* (2013.01); *A61B 5/4836* (2013.01); *A61B 5/6866* (2013.01); *A61B 5/7246* (2013.01); *G01J 4/04* (2013.01); *G01N 21/21* (2013.01); *A61B 2505/05* (2013.01); *A61B 2560/0233* (2013.01);
(Continued)

(58) Field of Classification Search
None
See application file for complete search history.

(56) References Cited

U.S. PATENT DOCUMENTS

| | | | | | |
|---|---|---|---|---|---|
| 5,798,837 | A * | 8/1998 | Aspnes | ............. | G01B 11/0641 356/369 |
| 7,245,952 | B2 * | 7/2007 | Cameron | ............. | A61B 5/14532 600/310 |
| 2011/0009720 | A1 * | 1/2011 | Kunjan | ............. | A61B 5/14532 600/316 |

* cited by examiner

Primary Examiner — Eric Winakur
Assistant Examiner — Marjan Fardanesh
(74) Attorney, Agent, or Firm — Cahill Glazer PLC

(57) ABSTRACT

Perioperative patient blood glucose concentrations are determined by imposing patient effluent ultrafiltrate through a sample cell incorporated in an automated polarimeter. The device includes an optical platform, fluid handling subassembly, controlling electronics, and integration software. A stable collimated light source of known intensity and distinct specified wavelength is passed through an optical platform including a polarizer, retarder, bandpass filters, sample flow cell, analyzer and detector. The angular rotation of the transmitted light resulting from the glucose contained in patient ultrafiltrate collected in the sample flow cell is recorded and provides a measure of the glucose concentration.

4 Claims, 6 Drawing Sheets

(51) Int. Cl.
*G01N 21/21* (2006.01)
*A61B 5/00* (2006.01)
*A61B 5/1459* (2006.01)
*A61B 5/15* (2006.01)
*A61B 5/155* (2006.01)
*A61B 5/1495* (2006.01)
*G01J 4/04* (2006.01)
*A61B 5/153* (2006.01)

(52) U.S. Cl.
CPC ............... *G01N 2201/062* (2013.01); *G01N 2201/0612* (2013.01); *G01N 2201/127* (2013.01)

METHOD AND APPARATUS FOR AUTOMATED MEASUREMENT OF CHIRAL ANALYTE CONCENTRATION

RELATED APPLICATIONS

This application is related to and claims priority to a provisional application entitled "METHOD AND APPARATUS FOR AUTOMATED MEASUREMENT OF CHIRAL ANALYTE CONCENTRATION" filed Jun. 5, 2012, and assigned Ser. No. 61/655,806.

FIELD OF THE INVENTION

The present invention relates to the measurement of physiological analytes and particularly to automated systems for the measurement of such analytes throughout major surgical procedures and the measurement of such analytes in the care of critically ill patients.

BACKGROUND OF THE INVENTION

The detrimental effects of elevated perioperative blood glucose have been reported in a large and growing body of peer-reviewed medical publications. Pre-operative and intraoperative hypoglycemia and hyperglycemia have been reported as independent risk factors for postoperative complications, including infection and death. In modern surgical suites there are limited space and personnel available for monitoring patient blood analytes, though studies have shown the importance for tightly controlled glucose during cardiothoracic and other major surgical procedures. The current method for monitoring patient blood glucose is to obtain a sample of the patient's blood and have it sent to the hospital lab for analysis, or to a nearby point-of-care laboratory system. These procedures lack sufficient accuracy, take too long, and require that limited staff take time away from critical functions to draw a blood sample, analyze it, or send it off to the hospital's lab for analysis (and wait for results). The time lag between sampling and delivery of results is detrimental to optimum blood glucose management.

The "Portland Protocol" (Furnary 2004), where insulin is continuously provided to the patient during open heart surgical procedures, was developed to keep blood glucose from rising above 180 mg/dL, but does not address hypoglycemic (low blood glucose) conditions that lead to other postoperative complications. Tight glucose control, targeting concentrations between 80-120 mg/dL has been shown in published studies to reduce postoperative complications. These complications include mediastinitis or deep sternal wound infection, loss of mental acuity, respiratory infections, and death. Reduced mortality, reduced morbidity, lower incidence of surgical site infections, enhanced long term survival, and reduction in lost mental acuity are benefits of maintaining blood glucose concentrations below 180 mg/dL. Of the seventy-five percent of patients that lose some mental acuity during surgery about 50% regain normal function over the next year. Hypoglycemia during surgery has been associated with this loss, and more frequent monitoring of patients before, during, and after surgery to maintain optimal blood glucose events will provide for faster healing and improved patient outcomes.

There are currently no automated blood glucose monitoring systems utilized to monitor critically ill patients or perioperatively. Some companies have developed implantable monitors for use in critical care settings, but none for intraoperative monitoring.

Prior art products include an implantable catheter that would be expected to add complexity to the number of attachment's (IV's, monitors, oxygen, etc.) to the patient. It is used in conjunction with an injectable compound that provides fluorescence in the presence of glucose. Little is known about how this might interact with the hemoconcentrator or heart-lung bypass process, in addition to a lack of measurement precision and sensitivity.

Another prior art product provides an implantable sensor that takes readings from interstitial fluid collected via microdialysis and transmits them via RFID to a monitor within five feet of the patient. It has received CE Mark as a Class II A medical device. It has been designed for use in clinical settings by healthcare professionals, but requires calibration with inaccurate and labor intensive fingerstick or laboratory analysis.

While continuous monitors based on microdialysis technologies for diabetic patients have been released to market in the United States, they are not stand-alone monitors, and require that the patient calibrate and make adjustments to treatment (insulin injection or medication) based on readings from old inaccurate existing finger-stick method and monitor, or confirmation readings from clinical laboratory devices.

The current method for measuring glucose during surgery is to draw a blood sample and send it to the hospital's lab for analysis and wait for results to be returned to the surgical suite. Time between testing and receipt of results can be more than an hour, and presumably because of this, patient sampling is done at least on an hourly basis during cardiothoracic surgeries that last on average about six hours, which does not provide sufficiently frequent measurement to permit timely adjustment of insulin and/or glucose.

Over the past decade, the occurrence of one of the worst postoperative complications, namely deep sternal wound infection, has been increasing. Rates that used to be 1% or less are now occurring in 2-3% of cases, and in some hospital systems in more than 4%. The incidence of diabetes, and therefore the number of diabetic patients undergoing surgery has increased, pushing mortality, morbidity, and hospitals costs upwards.

A variety of clinical procedures have been implemented that have helped slow the increase in the incidence of deep sternal wound infections, but none has addressed it as sufficiently as shown in the clinical studies over the past four years. These measures include antibiotic treatments, wound care solutions (platelet rich plasma), hand washing, and reduction of surgical personnel moving in and out of the surgical suite.

Microdialysis based continuous monitors remain targeted at the much larger consumer monitor market, and have not yet been applied successfully to perioperative monitoring, and continue to be used as ancillary products to track trends as opposed to adjusting or directing treatment, due to their lack of sufficient accuracy and necessary precision.

The prior art includes an injectable product that glows in the presence of glucose, however the results obtained are general in nature and not sufficiently specific to provide guidance in therapeutic treatment. Microdialysis based monitors incorporate a minimally invasive sensor that is implanted in the skin of the patient. Most utilize RFID or Bluetooth technology to transmit measurement data to the monitors, again with high costs and insufficient measurement precision.

The prior art also includes a number of devices that measure blood glucose, none of which has been applied to the specifications or the working environment found in cardiothoracic and other major surgeries, or intensive care units. Most require too much hands-on effort, frequent calibration, implantables, transmission radio frequencies, or other issues that would preclude their providing the required accurate, safe, convenient, and automated real-time measurement system that displays results on-demand.

Conventional methods for relatively crude industrial measurement of chiral analytes (sugars such as glucose) are shown in U.S. Pat. No. 3,411,342. This polarimeter consisted of a light source, collimating lens, a primary polarizer to establish a reference point for measurement of optical rotation, a sample cell through which a continuous stream of crude syrup was circulated, and a measuring circuit that determined the extent of optical rotation caused by the sample through an appropriate output signal. Visible light sources in the 400-700 nm wavelength were typical with this type of polarimeter. The minute concentrations of glucose that are present in the human body are far below the sensitivity provided by such polarimeters.

It is well known that glucose in solution is an optically active material. Due to its molecular structure it will cause the plane of polarization of light to be passing through the solution to be changed. The quantitative relationship between the amount of polarization rotation, the glucose concentration, and the length of the optical path through which the light travels has been clearly established. This is expressed mathematically as:

$$\Delta\theta = \alpha * L * C$$

Where:
- $\Delta\theta$ is the polarization change in degrees;
- $\alpha$ is the specific rotation constant dependent on the specified glucose type and the wavelength of the light source;
  - $\alpha$: 56.5 degrees per decimeter per gram per milliliter for a-d-glucose at a wavelength of 633 nanometers;
- L is the path length of the optical path containing the glucose solution in decimeters (dm) where (1 dm: 10 cm, or 10 centimeters); and
- C is the concentration of the glucose solution in grams (g) per 100 milliliters (ml) of solution or g/dL (from "Sugar Analysis" 3rd Edition, Browne & Zerban, John Wiley & Sons, 1941, page 263).

For the clinically meaningful glucose concentration of 40 to 400 mg/dL (milligrams per deciliter) and a path length of 5 cm (centimeters) the observed rotation ranges from about 0.0112° to 0.11275° for a wavelength of 633 nanometers (nm) As the wavelength of the light source is increased the specific rotation decreases, to a value of 26.3° per decimeter per gram per milliliter for a-d-glucose at a wavelength of 900 nanometers. At that wavelength the rotation in the above case is reduced to 0.0052 and 0.052° respectively.

If the assumption is made that there is about a 10% change in the optical transmission through the 5 cm path of a flow cell; then a 5 cm path length through the flow cell should produce about 0.0042 to 0.047° of polarization rotation. Thus, a usable system must have a basic sensitivity on the order of about 0.0042° degrees, i.e., 14 arc-second, or 70 microradians, with a 5 cm flow cell.

U.S. Pat. No. 5,209,231 by Cote, et al., describes a non-invasive glucose sensor which utilizes a pair of polarizers, a quarter wave plate, and a motor driven polarizer which produces a constant amplitude phase modulated beam. This beam is split into two beams, one of which passes through the sample and the other which is employed as a reference. By phase demodulation of the two beams, each incident on a different detector, a measure of glucose concentration in an optical cell is determined. Measurements are proposed to be made transversely through the eye's anterior chamber. This approach suffers in sensitivity of measurement (according to the authors) which is probably due to noise problems associated with the motor driven phase modulator as well as other unidentified problems.

"Multispectral Polarimetric Glucose Detection using a Single Pockels Cell", Optical Engineering, Vol. 33, pp 2746 (1994) by King, et al., describes a system which employs a pair of polarizers, a quarter wave plate, and a Pockels cell modulator which are configured as a polarization spectrometer. They employed the output from a lock-in amplifier which is "filtered using a leaky integrator" and then fed back to a compensator circuit which was eventually summed with the driver oscillator output and then input to the Pockels cell driver to null the AC signal in the system. Again, noise levels in the system represent the major problem in achieving the required sensitivity. The reported data show a scatter that is unacceptable for a working blood glucose sensor.

Similarly, Pockels cell modulation has been employed for differential analysis of chiral analytes in flow cells (U.S. Pat. No. 5,168,326). By applying oscillating voltage to the Pockels cell, alternating beams of circular and linearly polarized light are produced. Greater sensitivity is achieved through effectively removing noise by subtracting the rotation angles calculated for each of the beams.

The analysis techniques for chiral analytes such as glucose have been improved in the area of noise reduction. There are various single beam methods utilizing electronic or optical means to filter noise (as an example, WO 01/06918). Additional methods utilize dual beams either by comparison to a reference cell (U.S. Pat. No. 4,912,059), mixing out of phase sinusoidal signals (U.S. Pat. No. 5,477,327), switching between a signal and reference beam (U.S. Pat. No. 5,621,528), or using a two frequency laser source with two orthogonal linear polarized waves (U.S. Pat. Nos. 5,896,198 and 6,327,037). Glucose measurement is based on ascertaining the change in optical rotation (transmission) from the optical null point.

The inventor has developed patented prior art utilizing modulated sources (U.S. Pat. No. 6,999,808, U.S. Pat. No. RE39642, U.S. Pat. No. RE40316, and U.S. Pat. No. 6,370,407) demonstrating methods and devices for precisely extracting signals out of the noise, and provided greater sensitivity and stability than required. The methods therein described suffer from a common problem of cost and complexity that reduce their commercial utility from a practical standpoint.

Thus, there remains a need to provide a more practical, cost effective, and accurate automated method for quantifying the change in optical rotation introduced by a chiral analyte, such as glucose, by reducing the noise associated with the measurement and moving away from predictive mathematics in favor of direct measurement.

OBJECTS OF THE INVENTION

Accordingly, it is an object of the invention to provide a practical, reliable, affordable, and automated apparatus capable of accurately measuring the concentration of an optically active ingredient such as glucose in a sample.

It is another object of the invention to provide an automated device capable of accurately measuring the glucose concentration in a blood product acquired from patient blood before, during, and after major surgical procedures (perioperatively) and in critical care settings. During surgery, the device can monitor directly from ultrafiltrate effluent discharged from the hemoconcentrator without additional invasive measures or attachments to the patient (subject).

It is another object of this invention to provide a new very sensitive, stable, practical, and cost effective polarimeter which has applications in ellipsometry and in certain types of chemical analysis.

SUMMARY OF THE INVENTION

The present invention provides an innovative approach to generating and maintaining a very stable and robust monochromatic light source that incorporates a highly controlled level of emitted power intensity through intense and highly precise management of a plurality of electro-optical and thermal machine states. The signal provided from this source is utilized to make direct measurement of chiral analytes such as glucose without the need for predictive mathematics. Optimal operating conditions, as they relate to the measurement system as a whole, are maintained for each and every one of the mechanical, optical, thermal, and electro-optical components utilized in the system.

Briefly described, and in accordance with an embodiment chosen for illustration, the invention provides an automated system and method for measuring the concentration of an optically active substance, for example glucose, in a measurement cell incorporated in the apparatus, by guiding a beam, preferably of collimated monochromatic light, through a polarizer oriented in a first direction to polarize the light in a first direction, through a retarder, and then through a calibration cell (fluid filled or solid optic), and then through a measurement cell which is intermittently filled with sample ultrafiltrate, calibration standard, or flush solution having no chiral analyte concentration or having a known concentration of chiral analyte, and then through the second polarizer (analyzer) which is oriented in a second direction to polarize the light in a second direction. The beam is then guided from the analyzer to a detector. The optical platform is "aligned" when the polarizer, a retarder, and analyzer are adjusted to minimize the amount of light passing to the detector assembly that may optionally include line filters, focusing lenses, and/or bandpass filters. In preferred embodiments once the platform is aligned an optical bias is imposed on the signal by adjusting the retarder, or either increasing or decreasing the output power of the light source to provide a specified electronic response at the detector. This describes the optical path through which monochromatic light is passed to provide a signal to the detector that is utilized to provide a measure of the optical rotation caused by the chiral analyte(s) that are delivered into the measurement cell. As indicated above the degree of rotation is dependent on the concentration of the chiral analyte, the length of the measured optical path, the wavelength and intensity of the light source, the quality of extinction in the polarizers, and the type of retarder utilized (half-, quarter-wave plate, etc.).

In the embodiment chosen for illustration the retarder, preferably a quarter-wave plate, is adjusted to provide a predetermined optical bias at the detector. The difference between the amount of monochromatic light reaching the detector when a solution of known (or no) optical rotation is in the measurement cell and the amount that reaches the detector when passed through a sample represents the concentration of the glucose in the flow cell.

Alternatively, the optics may be adjusted to allow a maximum signal to reach the detector, and the reduction in signal received at the detector will represents the concentration of glucose in the flow cell.

The monochromatic light source in one embodiment is a laser diode or light emitting diode assembly with a known wavelength in the visual and near IR range. Applicant's system is presently designed for 635 nm. This specific wavelength was utilized to permit "off-the-shelf" optics; however, the system has successfully been operated at 780 nm although this range requires safety devices such as interlocks to protect operators. It was found that 780 nm wavelength provided much better transmission, with less rotation, but negligible interference. The light source assembly is equipped with feedback temperature controller to stabilize the light source. The required stability of the monochromatic source received by the detector allows for fluctuations totaling not more than four percent of the range of response for glucose concentrations from 0 mg to 400 mg/dL (dynamic range), and preferably an order of magnitude below. As an example for operating parameters with a dynamic range of 240 mV the tolerance for baseline fluctuations would be no greater than +/−5 mV.

The first polarizer is incorporated in the optical platform in front of the light source and is oriented to provide a specific state of polarized light. As in most polarimetry and ellipsometry the optical components are selected to match the wavelength of the light source, and the optics have anti-reflective coatings of the same wavelength mounted on their surfaces. The resolution of the degree to which the optical signal can be managed is highly dependent on the extinction ratios of the polarizers. In the preferred embodiment extinction ratios range between 1:10,000 and 1:100,000 are obtained. This is described as an optical component through which one part of light in 10,000 to 100,000 of the light is incident on the detector; for a very carefully oriented polarizer and analyzer system the transmission is about 1 part in 100,000. The utilization of a retarder further increases the precision by providing greater resolution of the signal of the basic polarimeter.

Sample ultrafiltrate, flush solution, or calibration standard of a known concentration of chiral analyte are delivered to the flow cell of the above described apparatus (polarimeter) by means of an electronic pump controlled by the device's operating software. The individual bags of aqueous calibration standard and flush solution, gas eliminating valves, check valves, connectors, tubing, ultrafilter, self loading pump heads, waste line, waste reservoir, IV cannulae, and pressure, flow, and bubble sensors may be provided as a disposable unit to be utilized for each patient undergoing surgery or in critical care settings where the apparatus is to be utilized.

BRIEF DESCRIPTION OF THE DRAWINGS

The present invention may more readily be described by reference to the accompanying drawings in which.

Figure 1:
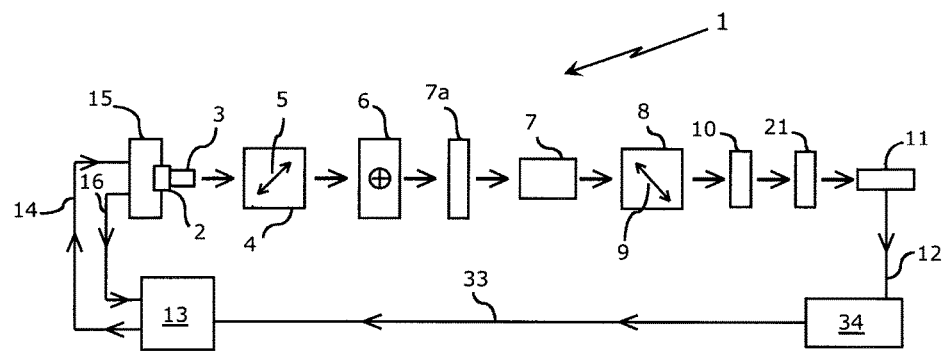
FIG. 1 is a schematic block diagram of an optical platform utilized in the system of the present invention.

In the drawings, bold lines interconnecting functional blocks indicate fluid connection such as blood, ultrafiltrate, and the like; light lines interconnecting functional blocks indicate electronic/electrical signal transmission.

DETAILED DESCRIPTION OF THE INVENTION

In one embodiment of the proposed device, light from a monochromatic source, such as an LED or laser diode, is collimated and polarized. This light beam is passed through a retarder and subsequently through a high quality optical quartz glass flow cell through which the sample ultrafiltrate, calibration standard or flush solvent are drawn by the device's pump and manifold system. The light emanating from the measurement flow cell is routed through the analyzer, and optionally through a focusing lens and/or bandpass filter of known wavelength, before it is directed onto the detector.

Referring to FIG. 1, a monochromatic light source (laser diode or light emitting diode) 2 is shown, the output of which is collimated by an optical component 3 (if needed) and transmitted to a polarizer 4. Applicant has found that the utilization of a 10 mW, 635 nm laser diode having an integrated, internal beam corrected optic is suitable. Double ended arrow 5 indicates the direction of polarization of light passing through polarizer 4.

The resulting linearly polarized light passes through a retarder such as quarter wave or half wave plate 6. The retarder 6 represents the capability of a quarter wave plate to modify the relative phases and or direction of polarized light to produce elliptically and/or circularly polarized light. The retarder 6 is followed by a calibration cell 7a that can be a flow cell, fluid filled cell, or solid optical cell providing a known specified signal at the detector. Applicant has found that a suitable solid optical cell is available from Meadowlark® or Rudolph Research®, or a flow cell from Hellma® may be utilized with suitable calibration fluid. The light emanating from the calibration cell 7a is passed through a measurement cell 7 through which the polarized light from the retarder and calibration cell 7a passes on the way to the analyzer 8. The double ended arrow 9 represents the direction of the polarization of light passing through of the analyzer 8. Light emanating from analyzer 8 passes through focusing lens 10 and/or bandpass filter 21 and is focused onto a suitable detector 11 such as a silicon photodiode which produces an output signal 12 that represents the amount of light that is transmitted through the entire polarimeter. A suitable detector 11 may be obtained from ThorLabs, part No. PD55. For a very carefully oriented polarizer, retarder, and analyzer system, the transmission should be less than 1 part in 100,000 of light incident on the detector.

In the embodiment shown in FIG. 1, an optical platform 1 is shown including a collimating component 3 that is incorporated with the light source 2, and along with a thermo-electric controller 15 (TEC) to form a light source assembly. Applicant has determined that the thermo-electric controller TEC produced by Wavelength Electronics, part No. WTC3243, is suitable for use in the present invention. The TEC 15 and light source 2 are managed through command signals 14 from the light source driver/controller 13, which are generated from feedback signals 12 received by the microprocessor 34 from the detector 11. A suitable light source driver may be obtained from Wavelength Electronics and designated LDD200-2P 200 mA laser driver. The microprocessor 34 sends signals 33 to the light source driver/controller 13 to precisely control the light source power output. This feedback loop increases or decreases the output power of the emitted light through signals driving the light source 2 in constant power mode to a specified level of electrical response at the detector. The stabilized monochromatic light emitted from the collimated component 3 is linearly polarized as it passes through the first polarizer 4 and elliptically/circularly polarized as it passes through the retarder 6. The rotational position of the first polarizer 4, retarder 6, and analyzer 8 are adjusted to provide the desired signal at the detector 11 with no chiral fluid in the measurement cell 7 or with chiral fluid having a known concentration of chiral analyte. This then will allow a measurement of the concentration of a chiral molecule (such as glucose) based on the change in the signal, when the glucose solution replaces the non-chiral fluid in the measurement cell. The optical platform includes the monochromatic light source 2, collimating element 3 (if needed), first polarizer 4, retarder 6, calibration cell 7a, measurement cell 7, analyzer 8, focusing lens 10 (if needed) and/or bandpass filter 21 (if utilized), and finally the detector 11. The first polarizer 4, retarder 6, analyzer 8 are readily available components and included a high precision polarizer and analyzer from Meadowlark® having an extinction ratio of 100,000 with a 635 nm anti-reflective coating. Similarly, the quarter wave plate was provided with a 635 nm anti-reflective coating.

During the initialization of the instrument, or setup, the retarder 6 and analyzer 8 are removed from the optical path and the first polarizer 4 is rotationally adjusted to provide the maximum signal at the detector 11. The analyzer 8 is then re-inserted in the optical path and adjusted to provide a minimum signal at the detector 11. The direction of polarization 9 of the analyzer 8 is perpendicular to the direction of polarization 5 of the first polarizer 4 (crossed polarizers concept). The retarder 6 is re-installed in the optical path and rotationally adjusted to minimize the intensity to approach extinction of the polarized light at the detector 11. The analyzer 8 is then adjusted to further minimize the intensity of light at the detector 11 followed by again adjusting the retarder. This process of adjusting the retarder 6 and analyzer 8 continues until the lowest intensity or extinction is obtained at the detector 11. Upon recognizing this level of light (known as "extinction") through the optical components at the detector 11, the resulting signal now takes into consideration all effects of light absorption, reflection, refraction, and transmission. The initialization procedure includes the alternative inverted procedure wherein the first adjustment is to obtain a minimum signal at the detector and the subsequent adjustments are made to obtain a maximum signal at the detector. Then the retarder 6 is adjusted to the desired baseline signal (or bias). Alternatively, the system can be adjusted to obtain a desired bias electronically by changing (increasing or decreasing) the power to the light source resulting in the desired baseline optical response (or bias) at the detector.

Figure 2:
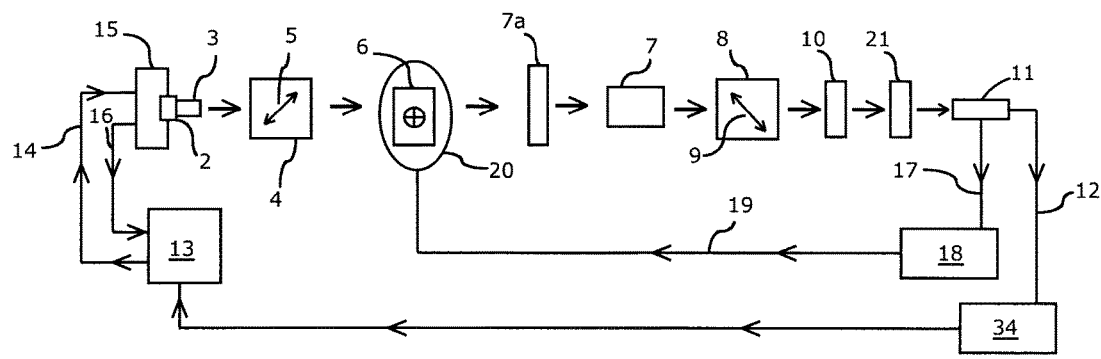
FIG. 2 is a schematic block diagram of a modified optical platform utilized in the system of the present invention incorporating an automated retarder stage.

Referring to the modification shown in FIG. 2, the retarder 6 (a quarter or half wave plate) is installed in an automated rotatory stage 20 in the optical path between the first polarizer 4 and the measurement cell 7. Through operating software the rotary stage 20 is rotated via automation to further extinguish light energy passing through the optical path to the detector 11. The retarder 6 mounted in rotatory stage 20, and the analyzer 8 are rotationally positioned (and locked in this "fixed" position) to allow the least amount of light possible to reach the detector 11. A suitable rotary stage is available from Newport® identified as Agilis® X-100. This minimizing of transmitted light is referred to as extinction, and is a function of the quality of the optics and the precision of the rotational positioning of the optical components.

Once "extinction" has been achieved, the retarder 6 is repositioned through the proposed device's operating software to provide a known baseline response (or bias) represented by a specified electronic signal at the detector 11. The retarder 6 is then locked in the position corresponding to the desired response bias. The optical platform is now optically aligned. In this embodiment the limiting factors are the quality of the polarizer 4, analyzer 8, and retarder 6, the precision of the retarder stage 20, the capability of determining the "position" of the intensity minimum (extinction) at the detector, and the ability of the light source driver/controller 13 to precisely maintain the intensity of the monochromatic light emitted from the light source 2 (that changes due to temperature change in the light source), and for the thermo-electric driver controller for the silicon photodiode detector to maintain the temperature of the detector. As temperature rises, frequency (wavelength) and/or intensity of the emitted light will change, as will the electronic response of the detector. It is imperative that stability of the light source and detector response be automatically maintained very precisely by the operating software.

In one embodiment, setting and management of the "baseline response" can be addressed with a retarder 6, that is set in a "fixed" position in its mount 20. In this iteration the signals 12 from the detector 11 would be received by the processor 34 that sends signals to the light source driver/controller 13 that sends signals to light source 2 to adjust the power output of the light source up or down to very precisely maintain the specified "baseline response" automatically between measurements.

Alternatively, the issue of "baseline" stability is addressed through software that manages and rotates a precision rotatory stage 20 rapidly and precisely through detector response feedback signals 17 received by the rotary stage driver controller 18 that sends command adjustment signals 19 to the rotatory stage 20 to re-establish the programmed baseline (or bias) between measurements.

In either of these alternative embodiments the measurement is then provided by the delta (change) in light energy received by the detector 11 as a function of the concentration of chiral analytes and the "baseline" response, and/or bias that is programmed into the operating software and maintained through automated adjustments. The "baseline" response is now maintained through a feedback loop that compensates for the intensity fluctuations of the light source, electrical "noise", and signal drift inherent in the system as temperatures change.

For calibration, referring to FIGS. 1 and 2, the calibration cell 7a is imposed in the optical platform 1 at a position between the retarder 6 and measurement cell 7. The calibration cell 7a can be a fluid filled optical cell (filled with a known concentration of chiral analyte), flow cell (filled with a known concentration(s) of chiral analyte), or optic capable of imposing rotation to the light passing through it equal to a known concentration of the analyte to be measured (glucose). The light passing through the calibration cell 7a and the measurement cell 7 filled with distilled water is received at the detector 11 providing an electronic signal equal to a known concentration of chiral analyte (glucose). This method provides a simplified calibration of the device where changes in the optical baseline are always accounted for during and between measurement cycles. The concentration of the chiral analyte (glucose) in the sample will always be relative to the response for the known concentration provided by the calibration cell regardless of potential changes in intensity that may impact the baseline response. As an example, a calibration cell providing rotation equal to 75 mg/dl, would provide an X response signal at the detector when distilled water is in the measurement cell, and that signal plus the response signal from the rotation for the sample or standard subsequently added to the measurement cell provides a measured value for the concentration of glucose in the measurement cell. That is, the concentration of glucose in the sample in the measurement cell would be a function of the response from the sample relative to the response from the calibration cell. For example:

Detector signal with calibration cell producing rotation equal to 75 mg/dL and DI in measurement cell=$X$ Signal produced when sample replaces DI in measurement cell=250% $X$ (2.5−1)75 mg/dL=112.5 mg/dL concentration of glucose in sample This method provides an externally manufactured calibration optic or component that can be imposed in the device for regulatory validation. Through this method the internal processor, thermal controller, light source driver, and detector feedback loops can be tested for their ability to maintain the system baseline response within expected specification limits for a known analyte concentration. The accuracy of measurement is then dependent solely on the system's ability to maintain that baseline response and addresses issues of "drift" that may occur during a measurement cycle. This calibration and measurement method provides a platform for direct measurement and moves the system away from the need for predictive measurements.

Figure 3:
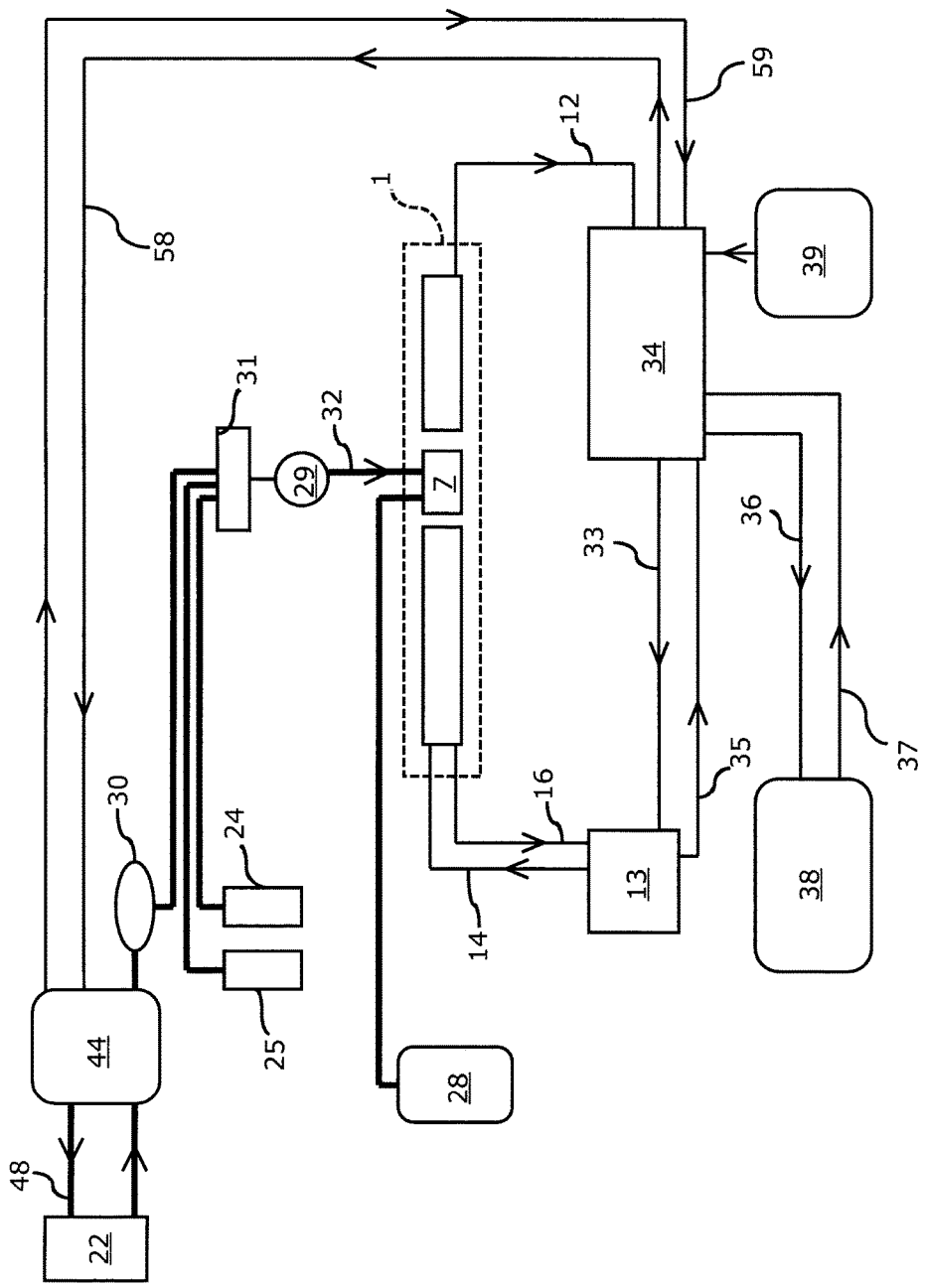
FIG. 3 is a schematic representation of the interconnections between subassemblies and components of a preferred embodiment of the invention.

Referring to FIG. 3, a schematic representation of the interconnections among components, including fluid flow systems and electrical signals, for a preferred embodiment is shown. The system includes the optical platform 1, the light source driver/controller 13, fluid handling pump 29 and manifold 31, sample pump manifold 44, and graphical user interface/display 38 that are managed by the processor 34. Blood from the patient or ultrafiltrate from other medical devices, such as a hemoconcentrator, dialysis machine, extracorporeal filtration unit referred to as the sample source 22, flows into a an ultrafilter 30.

In the case where the device is connected directly to a patient as the source 22, ultrafiltrate is removed from the patient's blood by the ultrafilter 30 via the sample pump manifold 44, and is directed to the measurement cell 7. The blood from the patient (source 22), minus a small quantity of serum ultrafiltrate may then returned to the patient via the patient return cannula 48. The system draws the ultrafiltrate through a main fluid manifold 31 being drawn (or pushed) by a pump 29 that fills the sample measurement cell 7 (it should be noted that the pump 29 can be incorporated either ahead of the flow cell to push fluid or after the flow cell to draw fluid through). The ultrafiltrate, flush solution supply 25, or calibration standard supply 24 is selectively directed through manifold 31 in accordance with the discrete operation selected by the user (and defined in the operating software). On demand, point in time, measurement is made of the analyte concentration in the patient ultrafiltrate through quantifying the rotation of the light energy passing through the optical platform 1 based on the amount of light energy that is captured by the detector 11 (FIG. 1). The system may be utilized in conjunction with the hemoconcentrator in open-heart surgery, extracorporeal filtration devices, hemodialyzers in dialysis and renal replacement therapy, or to be utilized as a stand-alone monitor connected directly to the patient.

Figure 4:
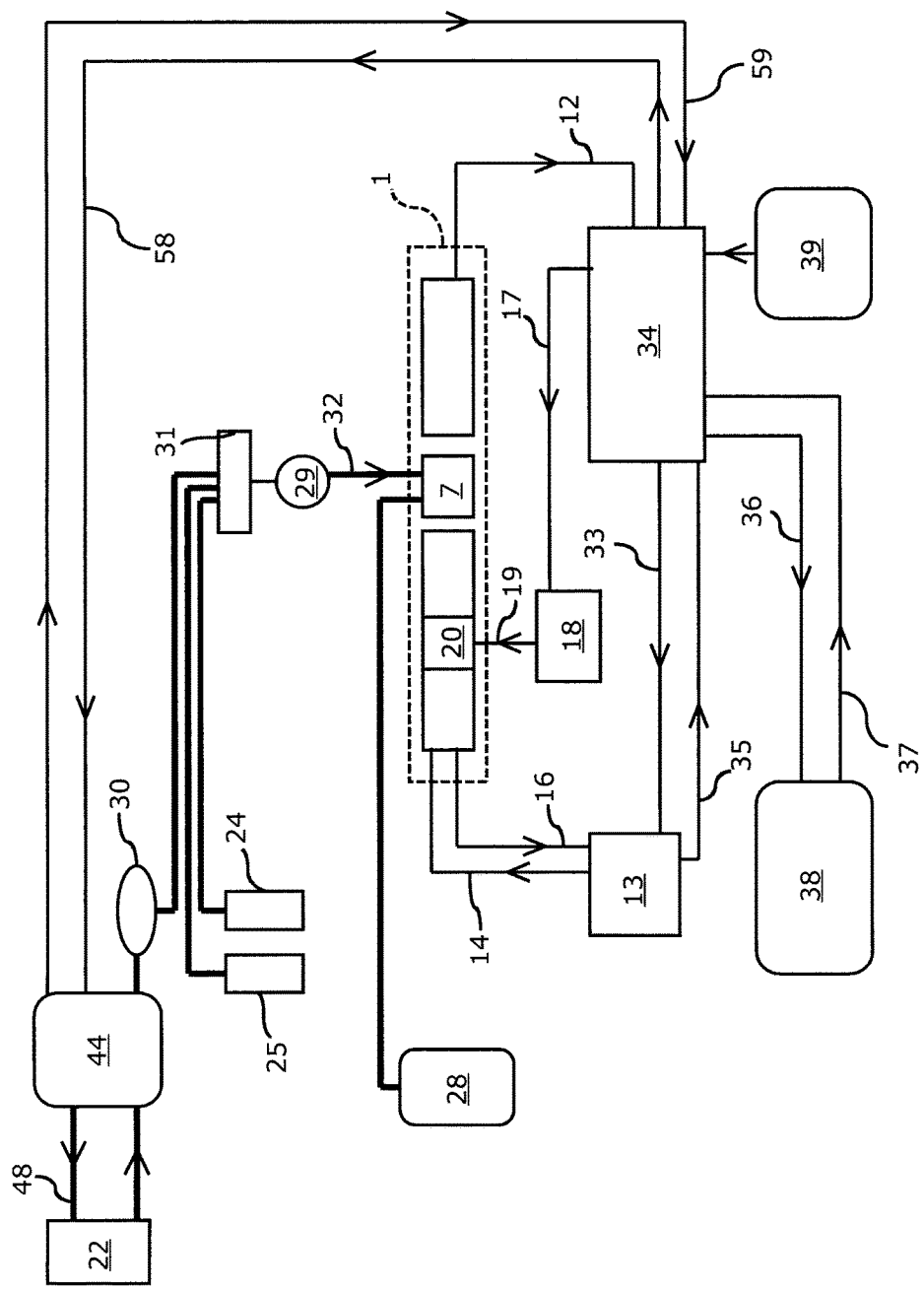
FIG. 4 is a schematic representation of the interconnections between subassemblies and components in an alternative embodiment of the present invention.

Referring to FIG. 4, is a schematic representation of the interconnections between sub-assemblies and components in an alternative embodiment is shown utilizing a rotary stage 20 and rotary stage driver 18 to maintain the response baseline. These include the optical platform 1, the light source driver/controller 13, rotatory stage driver/controller 18, fluid handling pump 29 and main fluid manifold 31, sample pump manifold 44, and graphical user interface/display 38 that are managed by the processor 34.

Blood from a patient undergoing open-heart surgical procedure on bypass (utilizing a heart-lung machine) flows through a hemoconcentrator. Ultrafiltrate originating at the hemoconcentrator has been removed from the patient's blood and is normally directed to a waste receptacle. The blood flows through the hemoconcentrator and is then directed to the heart-lung machine to be processed prior to being returned to the patient.

Inserting the present system into this procedure collects the waste ultrafiltrate at the sample source connection 22 and reroutes it through a secondary ultrafilter 30, and a main fluid manifold 31 being drawn (pushed) by a pump 29 that fills the sample measurement cell 7 selectively with ultrafiltrate, flush solution supply 25, or calibration standard supply 24 in accordance with the discrete operation selected by the user (and defined in the operating software).

On demand, point in time, measurement is made of the analyte concentration in the patient waste ultrafiltrate through quantifying the rotation of the light energy passing through the optical platform 1, based on the amount of light energy that is captured by the detector 11 (FIGS. 1 and 2).

For the polarizer to make discrete measurements, the status of a number of machine and components must be controlled and managed very precisely. The subsystems that must operate in precise reproducible unison and accord are the light source 2, light source thermo-electric temperature controller 15, light source driver/controller 13, rotatory stage 20 (if utilized), rotary stage driver 18 (if utilized), detector 11, graphical user interface 38, detector thermo-electric temperature controller 63 (if utilized—to be described) and detector driver/controller 64 (if utilized—to be described), multiple component power supplies 39, the sample pump manifold 44, the main fluid control manifold 31, main fluid control pump 29, and the on-board processor 34.

Figure 5:
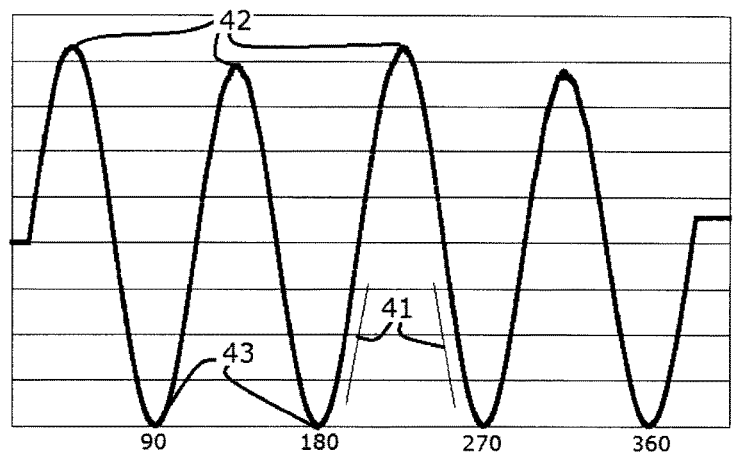
FIG. 5 is an illustration of the response amplitude of a quarter wave plate utilized as a retarder in the system of the present invention and useful in the description of the operation of the system.

Measurement is achieved by quantifying the optical rotation of the monochromatic light passing through chiral analytes such as glucose in solution. In one embodiment of the device, once the optics have been aligned as previously described to "extinction", an optical bias is applied by rotating the retarder 6 until the desired bias is achieved through the detector 11. In choosing the bias, an initial "slope" or "transmission curve" is plotted as shown in FIG. 5, and the peaks 42 and extinction points 43 noted. For a quarter wave plate retarder 6 there will be four peaks and extinction points. These peaks 42 and "valleys" 43 correspond to the fast and slow axes of the linearly polarized monochromatic light received from the first polarizer 4. If a half wave plate is employed as the retarder 6, there will be only two peaks and precision will be reduced by half.

FIG. 5 illustrates the four peaks from a quarter wave plate transmission curve. These are shown to illustrate the difference in response amplitude between the fast and slow axis. There are advantages to take measurements on either the upward or downward directed slopes of the fast axis. There will be 90° of rotation between extinction points 43 in a quarter wave plate, and 180° between these points for a half wave plate. In the preferred embodiment of the device, the bias is set at a preferred position above extinction on the upward slope of the fast axis 41. The optimum position in the slope provides the greatest linearity and dynamic range of the glucose measurements, though it must be noted that as the amplitude of the bias increases, there can be a proportional increase in noise. It is important to note that measurements can be taken on the upward or downward slope, with the most important aspects being dynamic range of the signal and the linearity of response within that range.

The system is driven and managed by appropriate operating software that monitors and manages the various machine states to maintain the stability of the baseline response; draw specified fluids through the device on demand; capture, process, and display data, manage calibration functions, and other processes. Silicon based photo-diode detectors provide a practical and cost effective component for capturing response data. Measurement accuracy and sensitivity are dependent on the stability of light sources and detectors that are temperature sensitive, it has been found that the control of temperature and management of drivers and controllers for these components by the operating software becomes critical.

Figure 6:
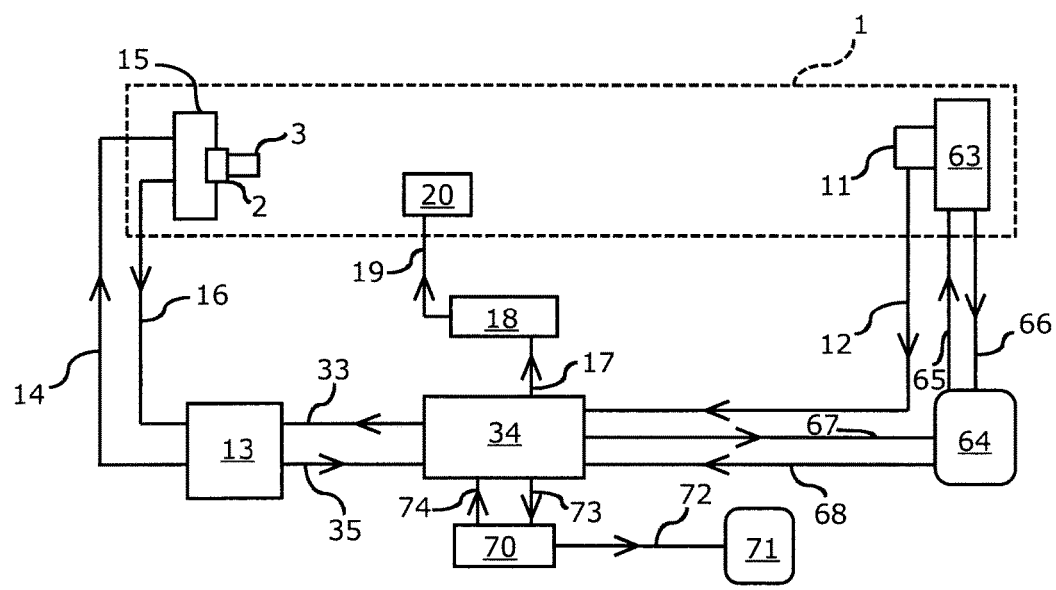
FIG. 6 is a schematic representation of information flow among components of the system of the present invention to facilitate description of the system operation.

Referring to FIG. 6, once the bias has been selected and set, the system software will maintain the intensity of the light source 2 through signals received by the light source driver/controller 13 from the processor 34 in response to signals 12 sent to said processor 34 by the detector 11, the end result of which are signals 33 sent to the light source driver/controller 13 to adjust the light source power up or down and initiates signals 14 to the light source temperature controller 15 to adjust the temperature of the light source. The processor 34 may at the same time be acting on signals 12 received from the detector 11, and sending signals 67 to the detector TEC driver controller 64 to adjust power to the detector TEC 63 to manage the temperature of the detector 11.

In an alternative embodiment using a rotary stage 20, the processor 34 is at the same time acting on the signals 12 received from the detector 11, and sending signals 17 to the rotatory stage controller 18 that sends signals to the rotatory stage 20 to rotate clockwise or counter clockwise to realign optically to the set bias, or "baseline" response. The feedback loops between detector, processor, light source driver/controller 13, and alternatively (or simultaneously) to the rotatory stage controller 18 provide a "baseline" controlling loop, ensuring that measurements are made as a function of the difference between the baseline and the rotation of the light in proportion to the concentration of glucose in the sample flow cell.

In a preferred embodiment the thermo-electric temperature controller 63 and controller driver 64 for the detector are managed via signals 67 and 68 provided to and from the system processor 34 and feedback signals 65 and 66 between the controller 63 and controller driver 64. An inline fluid heater/cooler 71 is imposed in fluid handling system to maintain constant temperature of fluids delivered to the measurement cell as the temperature of the sample affects measurement. The inline fluid heater/cooler 71 is managed through signals 72 from the inline fluid heater/cooler controller 70 that operates in response to signals to 74, and signals from 73 the processor 34. The various signals and operating parameters described are built into, and managed by the operating software.

Figure 7:
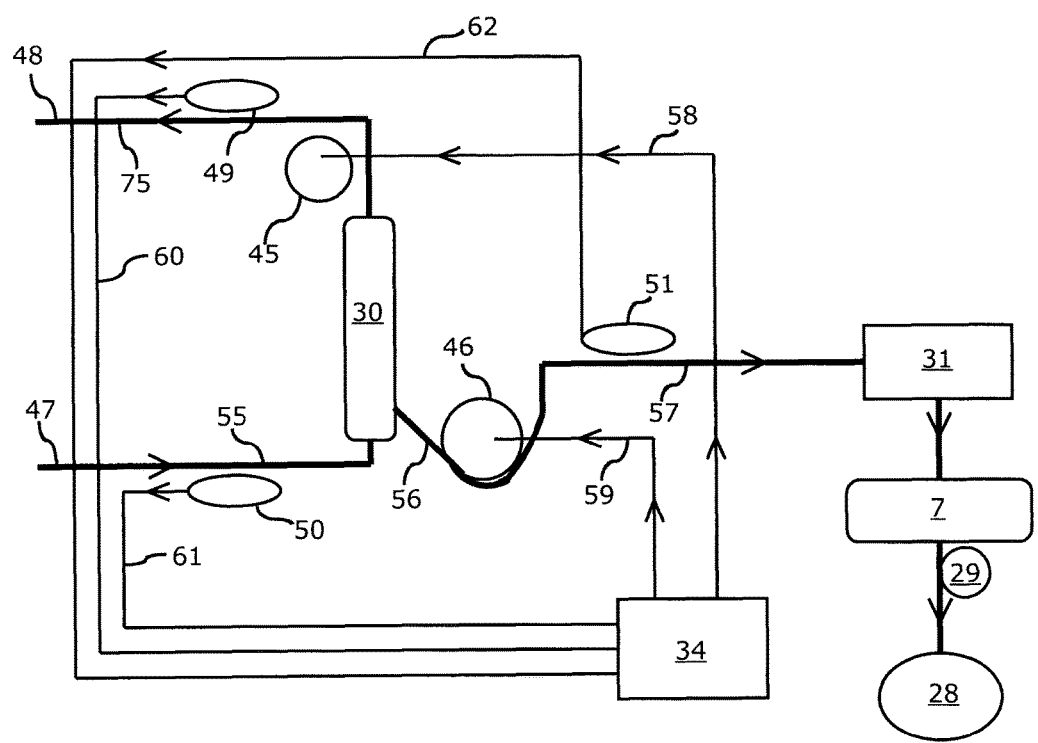
FIG. 7 is a functional flow diagram illustrating the interrelationship of fluid flow, sensors, and corresponding signals to and from the system processor.

FIG. 7 is a functional flow diagram illustrating the inter-relationship of fluid flow, sensors, and corresponding signals to and from the processor 34. The patient's ultrafiltrate from the system's ultrafilter 30 (which can be a hemodialyzer, hemoconcentrator, or other appropriately configured ultrafilter) is introduced to the main fluid manifold 31. The system includes a circulating pump 45, a vacuum pump 46, patient connector or intravenous draw catheter 47, an intravenous blood return catheter 48 an ultrafilter 30, patient pressure/flow sensors (draw and return) 49 and 50, vacuum line pressure/flow sensor 51, tubing 55 connecting catheter 47 to ultrafilter 30, tubing 56 connecting vacuum pump 46 to ultrafilter 30, and tubing 57 connecting vacuum pump 46 effluent to the main fluid handling manifold 31, as well as electronic connections between the pumps, sensors, power source, and main fluid handling manifold to the devices on board processor. In response to the appropriate signal 58 from the processor 34, the circulating pump 45 is engaged and begins to draw blood from the patient (or ultrafiltrate from other devices such as heart-lung effluent ultrafiltrate, extracorporeal filtration ultrafiltrate, dialysis ultrafiltrate, etc.).

Blood returning to the patient from the circulating pump 45 can be returned via a secondary intravenous catheter 48 or through existing IV lines entering the patient. After a predetermined time has passed to allow "priming" of the ultrafilter and patient blood return line, a signal 59 from the processor 34 is sent to the vacuum pump 46 which begins to draw ultrafiltrate from the ultrafilter 30.

In a preferred embodiment of the device the main fluid handling pump 29 may serve as the vacuum pump 46 to draw ultrafiltrate from patient blood or outside device effluent. This ultrafiltrate is delivered to the device's main fluid handling manifold 31 that sends it to the measurement cell 7 in response to signals from the processor 34 during a defined measurement cycle.

The patient draw 55 and return 75 lines can be flushed with a saline solution incorporating an anticoagulant. Sensor signals 61 from patient draw, signals 60 from patient return, and signal 62 from vacuum lines are provided to the processor 34 to maintain appropriate fluid flow without collapsing patient blood vessels, introducing bubbles to patient vascular system, or bubbles to the optical platform, as well as tracking fluid flow to the measurement cell. In the event of blockage or bubbles the processor would provide signals to disengage or reverse pumps. Signals 58 and 59 are provided to engage and disengage circulating pump 45 and vacuum pump 46 to provide ultrafiltrate samples to the optical platform.

Figure 8:
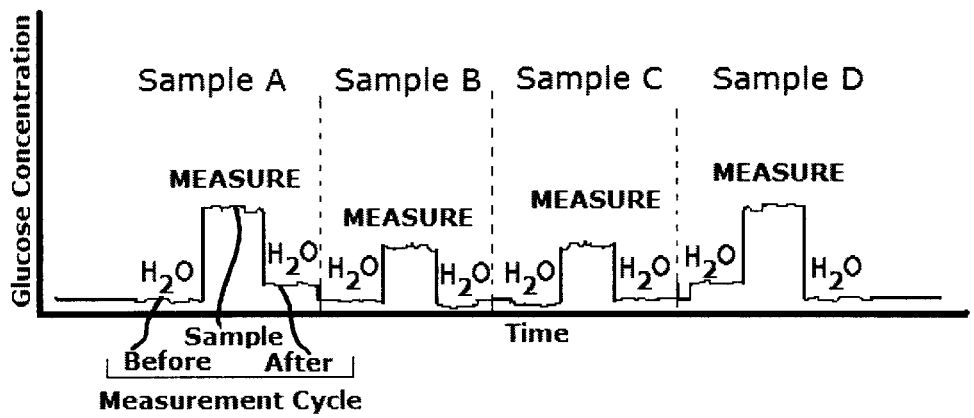
FIG. 8 is an illustration of the measurement method utilized in the present system to address the effects of drift in baseline response during the measurement cycle.

In the preferred embodiment of the device a baseline response is obtained by measurement through a solution of known (or no) optical rotation which produces known (or no) optical rotation characteristics. Discrete measurements are performed by the system's operating software, and incorporates three measurements for each displayed result (FIG. 8). The system takes a "baseline" reading of a solution of known (or no) optical rotation in the sample measurement cell 7 (FIG. 3), then a signal from the processor turns on the pump 29 and makes the manifold 31 adjustment for either the patient ultrafiltrate, or the calibration standard (in the event of a calibration run to confirm for example the accuracy of measurements being made or to modify settings to compensate for any variations). The pump 29 then draws fluid (patient ultrafiltrate or calibration standard supply 24) into the sample measurement cell 7, where it is allowed to dwell for a short period of time prior to taking readings of the amount of monochromatic light received by the detector. The pump 29 is then re-engaged and the manifold 31 selection set to flush solution supply 25 to flush the sample out of the cell and fill it with flush solution. After the sample measurement cell 7 has been flushed and is full, the fluid is allowed to "dwell" allowing all bubbles to clear the area where the monochromatic light passes through, and a second "baseline" reading is taken.

Referring to FIG. 8, two baseline readings are taken, and the difference between the average of the two baseline readings, one before sample measure and one after sample measure, and the readings taken for the patient ultrafiltrate or the calibration standard supply 24 provides the measure of the optical response representing the glucose concentration of the solution. This measurement method addresses "drift" in the baseline response during the measurement cycle. The software automatically returns the system to the specified baseline response (or bias) at the beginning of each measurement cycle. Referring to FIG. 8, the measurement method incorporated in the present invention is illustrated for four samples A-D. Baseline measurements are taken before and after each ultrafiltrate or calibration measurement; the before and after baseline measurements are averaged and the glucose concentration of the ultrafiltrate or calibration standard is then determined by reference to the average baseline reading.

When utilizing an in-line calibration cell 7a, measurements can alternatively be made as a function of the signal received at the detector 11 based on the rotation of the light passing through the calibration cell when a solution of known (or no) optical rotation 25 measurements are made and the measured response when calibration solution supply 24 or ultrafiltrate samples are in the measurement cell 7. As an example, the average sample measurement response divided by the average responses for a solution of known (or no) optical rotation before and after the sample measurement provides a percentage from which the calibration concentration can be subtracted to provide the concentration of the sample or standard corrected for "drift", as well as, shifts in emitted light frequency and/or intensity.

Figure 9:
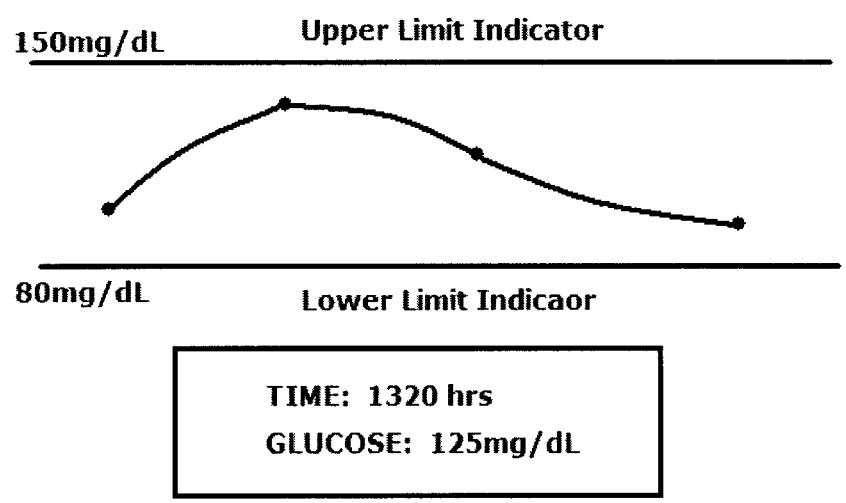
FIG. 9 is an illustration of a graphical user interface display employed in the system of the present invention showing trending of glucose measurements over time and the present glucose measurement and time.

The operating parameters may be entered into the graphical user interface (GUI) 38, which doubles as a display where glucose readings are displayed numerically and graphically as shown in FIG. 9. The display illustrated in FIG. 9 shows trending of the glucose measurements over time, and indicates whether or not the readings are within the glucose control levels programmed into the system as set by the medical professionals (between 80 mg/dL and 150 mg/dL).

It will be apparent to those skilled in the art that many commercial elements and off-the-shelf products are incorporated in the system of the present invention. For example, a variety of microprocessors may be found to be suitable; Applicant has determined that National Instruments microprocessor cRIO-9073 with Digital I/O, Analog I/O and Digital Capture Modules (part Nos. 9219, 9263 and 9474) were satisfactory for use in the present system. The programming of the microprocessor and controllers to perform the appropriate electronic functions, including control and monitoring of the system, is well known to those skilled in the art and need not be described here.

The present invention has been described in terms of selected specific embodiments of the apparatus and method incorporating details to facilitate the understanding of the principles of construction and operation of the invention. Such reference herein to a specific embodiment and details thereof is not intended to limit the scope of the claims appended hereto. It will be apparent to those skilled in the art that modifications may be made in the embodiments chosen for illustration without departing from the spirit and scope of the invention.

What is claimed:

1. A method for initializing apparatus for measuring the concentration of a chiral analyte, the apparatus including an optical platform having an optical path and having the following elements positioned in said optical path:
   (a) a light source of monochromatic light;
   (b) a first polarizer positioned to receive monochromatic light from said light source and having a direction of polarization;
   (c) a retarder positioned to receive polarized light from said first polarizer;
   (d) a calibration cell positioned to receive light from said retarder;
   (e) a measurement cell for selectively receiving a flush solution, distilled water, or a solution whose concentration of chiral analytes are to be measured, said measurement cell positioned to receive polarized light from said retarder;
   (f) an analyzer positioned to receive light from said measurement cell and having a direction of polarization perpendicular to the polarization of said first polarizer; and
   (g) a detector for receiving light from said analyzer and generating an electrical signal proportional to the light striking the detector;
the method comprising:
   (h) directing a beam of monochromatic light from said light source through said first polarizer, retarder, calibration cell, measurement cell, analyzer, onto said detector;
   (i) removing said analyzer and retarder from said optical light path;
   (j) rotationally adjusting said first polarizer to provide a maximum signal at said detector;
   (k) reinstalling said analyzer;
   (l) adjusting said analyzer to provide a minimum signal at said detector;
   (m) reinstalling said retarder in said optical path;
   (n) rotationally adjusting said retarder to further minimize the intensity of polarized light at said detector;
   (o) repeating steps (l) and (n) until the lowest intensity or extinction is obtained at the detector; and
   (p) adjusting the retarder to a determined baseline to provide a bias signal at said detector.

2. A method for initializing apparatus for measuring the concentration of a chiral analyte, the apparatus including an optical platform having an optical path and having the following elements positioned in said optical path:
   (a) a light source producing a beam of monochromatic light having a given intensity;
   (b) a first polarizer positioned to receive monochromatic light from said light source and having a direction of polarization;
   (c) a retarder positioned to receive polarized light from said first polarizer;
   (d) a calibration cell positioned to receive light from said retarder;
   (e) a measurement cell for selectively receiving a flush solution, distilled water, or a solution whose concentration of chiral analytes are to be measured, said measurement cell positioned to receive polarized light from said retarder;
   (f) an analyzer positioned to receive light from said measurement cell and having a direction of polarization perpendicular to the polarization of said first polarizer; and
   (g) a detector for receiving light from said analyzer and generating an electrical signal proportional to the light striking the detector;
the method comprising:
   (h) directing a beam of monochromatic light from said light source through said first polarizer, retarder, calibration cell, measurement cell, analyzer, onto said detector;
   (i) removing said analyzer and retarder from said optical light path;
   (j) rotationally adjusting said first polarizer to provide a maximum signal at said detector;
   (k) reinstalling said analyzer;
   (l) adjusting said analyzer to provide a minimum signal at said detector;
   (m) reinstalling said retarder in said optical path;
   (n) rotationally adjusting said retarder to minimize the intensity of polarized light at said detector;
   (o) repeating steps (l) and (n) until the lowest intensity or extinction is obtained at the detector; and
   (p) adjusting the light source intensity to provide a baseline or bias signal level at said detector.

3. A method for initializing apparatus for measuring the concentration of a chiral analyte, the apparatus including an optical platform having an optical path and having the following elements positioned in said optical path:
   (a) a light source of monochromatic light;
   (b) a first polarizer positioned to receive monochromatic light from said light source and having a direction of polarization;
   (c) a retarder positioned to receive polarized light from said first polarizer;
   (d) a calibration cell positioned to receive light from said retarder;
   (e) a measurement cell for selectively receiving a flush solution, distilled water, or a solution whose concentration of chiral analytes are to be measured, said measurement cell positioned to receive polarized light from said retarder;
   (f) an analyzer positioned to receive light from said measurement cell and having a direction of polarization perpendicular to the polarization of said first polarizer; and (g) a detector for receiving light from said analyzer and generating an electrical signal proportional to the light striking the detector;

the method comprising:

(h) directing a beam of monochromatic light from said light source through said first polarizer, retarder, calibration cell, measurement cell, analyzer, onto said detector;

(i) removing said analyzer and retarder from said optical light path;

(j) rotationally adjusting said first polarizer to provide a minimum signal at said detector;

(k) reinstalling said analyzer;

(l) adjusting said analyzer to provide a maximum signal at said detector;

(m) reinstalling said retarder in said optical path;

(n) rotationally adjusting said retarder to further maximize the intensity of polarized light at said detector;

(o) repeating steps (l) and (n) until the highest intensity is obtained at the detector; and (p) adjusting the retarder to a determined baseline to provide a bias signal at said detector.

4. A method for initializing apparatus for measuring the concentration of a chiral analyte, the apparatus including an optical platform having an optical path and having the following elements positioned in said optical path:

(a) a light source producing a beam of monochromatic light having a given intensity;

(b) a first polarizer positioned to receive monochromatic light from said light source and having a direction of polarization;

(c) a retarder positioned to receive polarized light from said first polarizer;

(d) a calibration cell positioned to receive light from said retarder;

(e) a measurement cell for selectively receiving a flush solution, distilled water, or a solution whose concentration of chiral analytes are to be measured, said measurement cell positioned to receive polarized light from said retarder;

(f) an analyzer positioned to receive light from said measurement cell and having a direction of polarization perpendicular to the polarization of said first polarizer; and (g) a detector for receiving light from said analyzer and generating an electrical signal proportional to the light striking the detector;

the method comprising:

(h) directing a beam of monochromatic light from said light source through said first polarizer, retarder, calibration cell, measurement cell, analyzer, onto said detector;

(i) removing said analyzer and retarder from said optical light path;

(j) rotationally adjusting said first polarizer to provide a minimum signal at said detector;

(k) reinstalling said analyzer;

(l) adjusting said analyzer to provide a maximum signal at said detector;

(m) reinstalling said retarder in said optical path;

(n) rotationally adjusting said retarder to maximize the intensity of polarized light at said detector;

(o) repeating steps (l) and (n) until the highest intensity is obtained at the detector; and (p) adjusting the light source intensity to provide a baseline or bias signal level at said detector.

* * * * *